US010539708B2

(12) United States Patent
Zhou et al.

(10) Patent No.: US 10,539,708 B2
(45) Date of Patent: Jan. 21, 2020

(54) MOBILE AND FREE-FORM X-RAY IMAGING SYSTEMS AND METHODS

(71) Applicant: The University of North Carolina at Chapel Hill, Chapel Hill, NC (US)

(72) Inventors: Otto Z. Zhou, Chapel Hill, NC (US); Jianping Lu, Chapel Hill, NC (US); Pavel Chtcheprov, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 436 days.

(21) Appl. No.: 15/587,052

(22) Filed: May 4, 2017

(65) Prior Publication Data
US 2017/0329037 A1    Nov. 16, 2017

Related U.S. Application Data

(63) Continuation-in-part of application No. 15/421,869, filed on Feb. 1, 2017.
(Continued)

(51) Int. Cl.
*G01V 5/00* (2006.01)
*G01N 23/046* (2018.01)
(Continued)

(52) U.S. Cl.
CPC ......... *G01V 5/0066* (2013.01); *G01N 23/046* (2013.01); *G01V 5/005* (2013.01);
(Continued)

(58) Field of Classification Search
CPC .... G01V 5/0025; G01V 5/0041; G01V 5/005; G01V 5/0058; G01V 5/0066; G01V 5/0083; B64C 39/024; B64C 2201/123; B64C 2201/127; B64D 47/08; G06T 2207/10032; G06T 2207/10116;
(Continued)

(56) References Cited

U.S. PATENT DOCUMENTS 5,241,578 A    8/1993   MacMahon
9,782,136 B2  10/2017   Zhou et al.
(Continued)

OTHER PUBLICATIONS

Non Final Office Action for U.S. Appl. No. 15/421,869 dated Aug. 22, 2019
(Continued)

*Primary Examiner* — Anastasia Midkiff
(74) *Attorney, Agent, or Firm* — Jenkins, Wilson, Taylor & Hunt, P.A.

(57) ABSTRACT

A three-dimensional (3D) x-ray tomographic imaging system includes an x-ray source fixedly attached to a first unmanned vehicle, which can be aerial or otherwise configured for locomotion, and an x-ray detector. A vehicle controller is configured to be operated by an operator, and an optical camera is mounted to the first unmanned vehicle at a fixed position relative to the x-ray source, and an optical pattern is fixed at a position relative to the x-ray detector. The x-ray source and x-ray detector are configured to be positioned on substantially opposite sides of the object, while the x-ray source is rotated radially around the object to one or more imaging positions.

22 Claims, 7 Drawing Sheets

Related U.S. Application Data

(60) Provisional application No. 62/331,746, filed on May 4, 2016, provisional application No. 62/289,714, filed on Feb. 1, 2016.

(51) Int. Cl.
  *H01J 37/244* (2006.01)
  *B64C 39/02* (2006.01)
  *B64D 47/08* (2006.01)

(52) U.S. Cl.
  CPC .......... *G01V 5/0025* (2013.01); *G01V 5/0083* (2013.01); *H01J 37/244* (2013.01); *B64C 39/024* (2013.01); *B64C 2201/123* (2013.01); *B64C 2201/127* (2013.01); *B64D 47/08* (2013.01); *G01N 2223/303* (2013.01); *G01N 2223/3037* (2013.01); *G01N 2223/419* (2013.01); *G01V 5/0041* (2013.01); *G06T 2207/10032* (2013.01); *G06T 2207/10116* (2013.01); *H01J 2237/1501* (2013.01); *H01J 2237/2482* (2013.01); *H01J 2237/24578* (2013.01)

(58) Field of Classification Search
  CPC ............. G01N 23/046; G01N 2223/30; G01N 2223/302; G01N 2223/303; G01N 2223/3035; G01N 2223/3037; G01N 2223/323; G01N 2223/34; G01N 2223/419; H01J 35/14; H01J 35/153; H01J 37/00; H01J 37/02; H01J 37/22; H01J 37/244; H01J 2237/00; H01J 2237/15; H01J 2237/1501; H01J 2237/1502; H01J 2237/1504; H01J 2237/245; H01J 2237/24507; H01J 2237/24514; H01J 2237/24528; H01J 2237/24578; H01J 2237/24592; H01J 2237/248; H01J 2237/2482; G01T 1/2978; G01T 7/00; G01T 7/005
  See application file for complete search history.

(56) References Cited

U.S. PATENT DOCUMENTS

| | | | |
|---|---|---|---|
| 9,907,520 | B2 | 3/2018 | Zhou et al. |
| 2002/0041655 | A1 | 4/2002 | Mitschke |
| 2009/0041201 | A1 | 2/2009 | Wang et al. |
| 2014/0221824 | A1 | 8/2014 | Rai et al. |
| 2015/0230768 | A1* | 8/2015 | Belei ............... A61B 6/463 378/62 |
| 2016/0106382 | A1 | 4/2016 | Lu et al. |
| 2016/0325835 | A1* | 11/2016 | Abuelsaad ....... G08G 1/096716 |
| 2017/0085867 | A1* | 3/2017 | Baran ............... H04N 13/122 |
| 2017/0219498 | A1 | 8/2017 | Chtcheprov |

OTHER PUBLICATIONS

Dobbins III, J.T., et al., "Digital x-ray tomosynthesis: current state of the art and clinical potential," Phys. Med. Biol. 48, pp. R65-R106 (2003).

Gauntt, D.M., et al., "An automatic and accurate x-ray tube focal spot/grid alignment system for mobile radiography: System description and alignment accuracy," Med. Phys. 37:12, pp. 6402-6410 (2010).

Miao, H., et al., "A phantom-based calibration method for digital x-ray tomosynthesis," J. X-Ray Sci. Technol. 20, pp. 17-29 (2012).

Qian, X., et al., "High resolution stationary digital breast tomosynthesis using distributed carbon nanotube x-ray source array," Med. Phys. 39:4, pp. 2090-2099 (2012).

Shan, J., et al., "Stationary chest tomosynthesis using a CNT x-ray source array," Proc. SPIE Medical Imaging, vol. 8668, pp. 86680E 1-12 (2013).

Svahn, T.M., et al., "Breast tomosynthesis and digital mammography: a comparison of diagnostic accuracy," Br. J. Radiol., 85, pp. e1074-e1082 (2012).

Tingberg, A., "X-ray tomosynthesis: a review of its use for breast and chest imaging," Radiat. Prot. Dosimetry, vol. 139, No. 1-3, pp. 100-107 (2010).

\* cited by examiner

MOBILE AND FREE-FORM X-RAY IMAGING SYSTEMS AND METHODS

CROSS-REFERENCE TO RELATED APPLICATIONS

This patent application claims priority to U.S. Provisional Patent Application Ser. No. 62/331,746, filed May 4, 2016, and this application is a continuation-in-part from and claims priority to pending U.S. patent application Ser. No. 15/421,869, filed Feb. 1, 2017 which claims priority to U.S. Provisional Patent Application Ser. No. 62/289,714 filed Feb. 1, 2016, the disclosures of which are both incorporated herein by reference in their entireties.

TECHNICAL FIELD

The subject matter disclosed herein relates to x-ray radiography, x-ray computed tomography (CT), and backscattering. More particularly, the subject matter disclosed herein relates to remotely controlled x-ray imaging systems and methods that are carried by either an unmanned aerial vehicle (UAV, e.g., a "drone") or an unmanned vehicle (UV) to produce tomosynthesis, CT, or backscatter images.

BACKGROUND

X-ray imaging is a useful tool to identify unknown objects. It is often used for the detection of explosives and contraband in situations where it is impractical or unsafe to move the object being imaged. Simple transmission imaging and backscattering imaging methods have been utilized for such "field" applications. Additionally, CT scanners have been installed in fixed locations, such as airports, for enhanced security screening.

Modern CT scanners typically use an x-ray tube and a digital detector mounted on a gantry. The x-ray tube and digital detector move around the gantry to collect a series of images which are used for image reconstruction Once the images are acquired, image reconstruction requires knowledge of precise locations of an x-ray source and an x-ray detector with respect to the object being imaged for each projection view taken.

Stationary CT and tomosynthesis scanners are also known. These scanners are referred to as "stationary" because of the use of an array of x-ray sources spatially distributed in a fixed pattern. The individual projection images are taken by activating the individual x-ray sources without moving the x-ray source or the detector.

While the process works reasonably well for systems installed in dedicated spaces, it becomes cumbersome and often impractical for mobile and field operations. The heavy mechanical gantry needed for mechanical stability takes up space and makes it difficult to design mobile tomography scanners that can be useful in situations where the patient cannot be easily transferred. Additionally, a fixed trajectory limits the imaging to simple acquisition geometry such as linear or circular arc acquisition due to practical engineering constraints, which may not provide the most efficient projection image set for every object and application.

Where x-ray imaging is being utilized for explosive detection in the field (e.g., in a public location), it is necessary for the imaging equipment to be placed adjacent to the object being imaged, but for the operator to be positioned remotely in order to ensure the safety of the operator in case of detonation. In such instances, the images can be transmitted through any of a number of wireless communication protocols.

A prior art portable x-ray imaging system is shown in FIG. 1, which includes, for example, a battery-powered x-ray source, generally designated 10, a flat panel x-ray detector, generally designated 20, and a wireless transmission device, generally designated 30. In such systems, the operator must place the x-ray detector and the x-ray source adjacent to the object, exposing the operator to potential danger from an explosion during placement of these system components. Some portable x-ray imaging systems attempt to address this by placing the x-ray source and the detector on an unmanned rover, generally designated 50, such as is shown in FIG. 2, that is then remotely driven to the object of interest to generate the x-ray images. As such, the currently known portable x-ray imaging systems are either carried by an operator or positioned by a ground vehicle.

At present, there exists a need for a convenient way to remotely obtain CT images of an object away from a fixed installation site (e.g., an airport). CT technology provides valuable three-dimensional ("3D") images of the internal structure of an object, removing overlapping, and providing better diagnosis compared to conventional two-dimensional ("2D") x-ray image. Dual energy CT data also enables chemical identification for determination of the presence of explosives, and can even differentiate between types of explosives. Dual energy CT is currently used in airports for inspection of checked baggage. As such, a remote-controlled CT scanner capable of generating a 3D image of an object without being physically transported to the object by the operator is highly desirable.

SUMMARY

It is an object of the subject matter herein to provide systems, devices, and methods such as those disclosed herein that can perform x-ray imaging and x-ray computed tomography (CT) imaging using a decoupled x-ray source and x-ray detector without a rigid gantry or a predetermined source-detector trajectory. For example, a remotely controlled x-ray imaging system that is carried by either a unmanned aerial vehicle (UAV, e.g., a "drone") or an unmanned vehicle (UV) that is configured to capture x-ray projection images of an object from multiple directions, determining the imaging geometries, transmitting the images wirelessly to a base station near the operator; and reconstructing the images into either tomosynthesis, CT or backscatter images, is provided.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described herein below.

DETAILED DESCRIPTION

Figure 1:
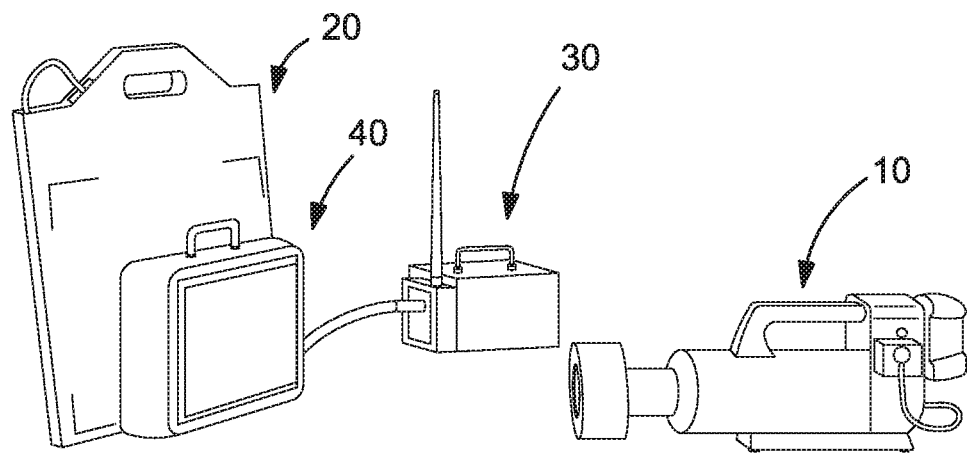
FIG. 1 shows a mobile x-ray imaging system known according to the prior art.
Figure 2:
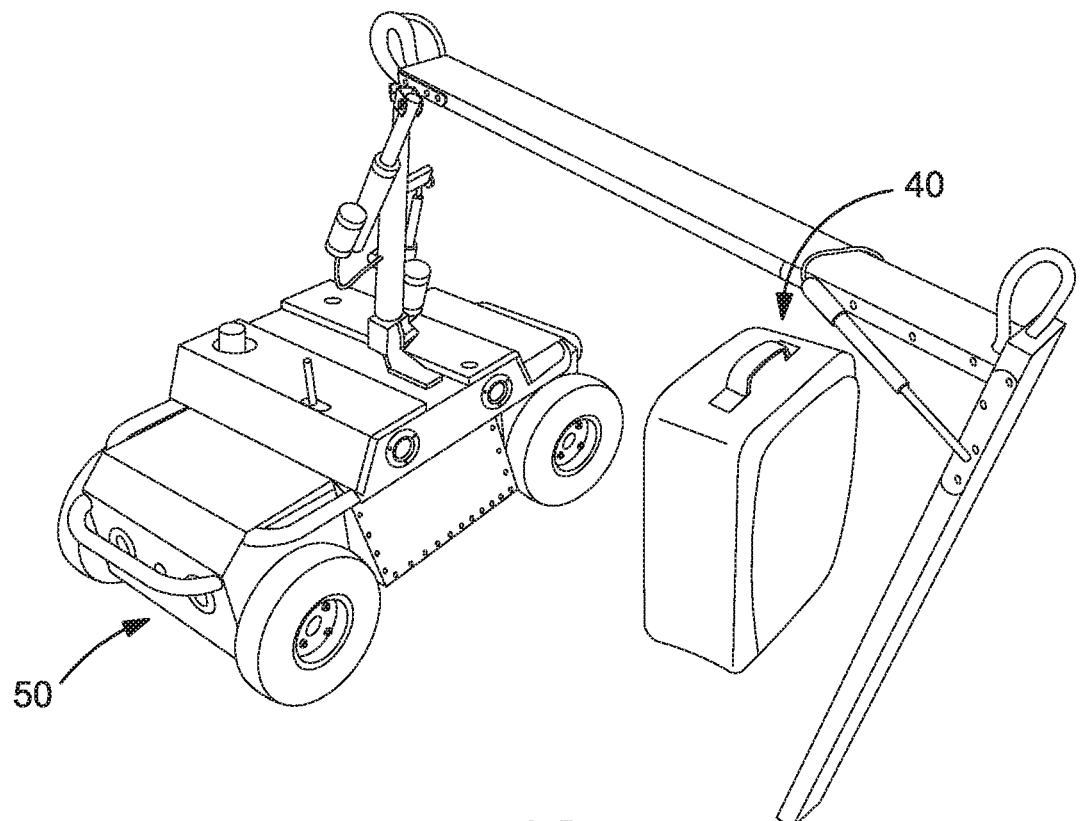
FIG. 2 shows a second embodiment of a mobile x-ray imaging system known according to the prior art.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

The terminology used herein is for the purpose of describing particular embodiments only, and is not intended to be interpreted as in any way limiting the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a tool" includes a plurality of such tools, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D. In traditional three-dimension x-ray tomography imaging devices, systems, apparatuses, assemblies, setups, etc., a position of an x-ray detector relative to x-ray source(s) is always known due to prior calibrations and its fixed position(s), such that geometry of the detector relative to the source(s) does not need to be determined for each data acquisition. By contrast, in a free-form setup for a tomography imaging device, system, apparatus, assembly, etc., a detector can be in any position(s) relative to a source(s) and be moved from image to image, where relative positions of the source(s) with respect to the detector need to be determined for each projection image.

Systems, devices, and methods disclosed herein are able to accomplish such a determination in a free-form manner. In some aspects, single or a plurality of x-ray images alone may be used. In some embodiments a phantom or other marker is placed on the object, and two images per position may be captured, one for calibration and another for the image set.

Figure 3:
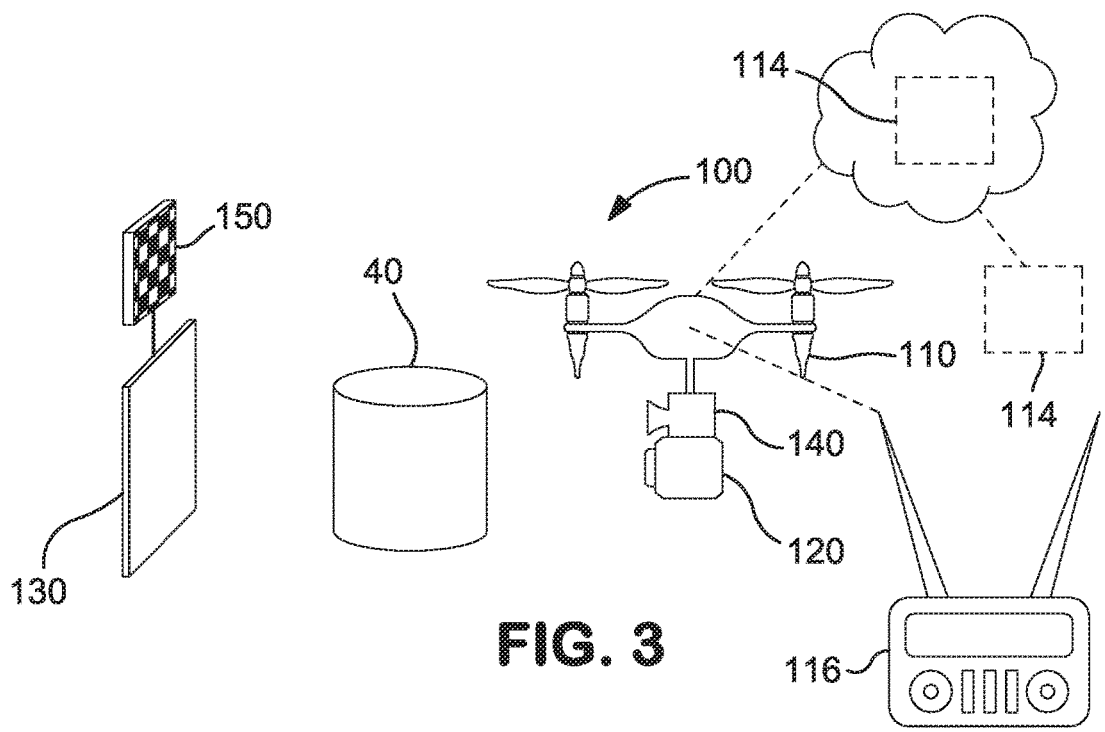
FIG. 3 is a schematic illustration of an example embodiment of an aerial mobile x-ray imaging system for computed tomography image reconstruction, in accordance with the disclosure herein.

Referring now to FIG. 3, a first example embodiment of a mobile aerial x-ray imaging system, generally designated 100, is shown. Imaging system 100 includes at least one unmanned aerial vehicle (UAV), generally designated 110; such UAVs are also commonly referred to as "drones". UAV 110 has an x-ray source 120 fixedly mounted thereon. While shown being located underneath UAV 110, x-ray source 120 may be located in any suitable position relative to UAV 110. X-ray source 120 is powered by a battery, which can be shared with the UAV. Additionally, x-ray source 120 can be controlled remotely through wireless signals from an operator terminal (e.g., a remote controller). UAV 110 is positioned on one side of an object 40, while an x-ray detector 130 is arranged at least substantially diametrically opposite (e.g., greater than 135° around object 40) x-ray source 120. X-ray detector 130 shown is a flat panel detector, but any suitable detector type and shape may be utilized. In some embodiments, x-ray detector 130 is photon activated. X-ray detector 130 is either in electronic communication with a wireless communication module or is itself capable of transmitting the x-ray images captured during activation of x-ray source 120 to an operator terminal via any suitable wireless communication protocol (e.g., Wi-Fi®, Bluetooth®, RF, etc.).

UAV 110 also has an optical camera that is, in some embodiments, attached at a fixed and predetermined position relative to x-ray source, so that the known geometric relationship between x-ray source 120 and optical camera 140 can be used during image reconstruction to de-skew the x-ray images captured by x-ray detector 130. In some other embodiments, optical camera 140 can be mounted, either directly or indirectly (e.g., via a linkage bar), to x-ray source 120. In still other embodiments, optical camera 140 can be a camera that is integral to UAV 110. In embodiments where optical camera 140 is integral with UAV 110, optical camera can be configured to be rotationally fixed or mobile. Where rotationally mobile, optical camera 140 is able to rotate radially over a predefined angular range (e.g., 90°, 180°, 270°, and/or 360°) so that optical pattern 150 is maintained within the field of vision of optical camera 140. Where optical camera 140 is configured to rotate radially with respect to an orientation of UAV 110, the angular position at which optical camera 140 is angled must be known relative to UAV 110 and/or x-ray source 120, so that this relative angular position can be used for geometric image correction (e.g., de-skewing) of the x-ray projection images captured.

To image an object, UAV 110 is moved by an input received by a vehicle controller 116, either manually or via software (e.g., via software executed by an artificial intelligence controller) and one or more distance sensors, to be located proximate to object 40. Such an artificial intelligence controller can be located, for example, remote from UAV 110 (e.g., on a cloud computing device) or onboard UAV 110. UAV 110 is configured to use the distance sensor to detect a distance from UAV 110 to object 40 and/or x-ray detector 130 so that UAV 110 can maintain a substantially consistent distance (e.g., the distance is measured to be accurate to within 1 mm, 5 mm, 10 mm, and/or 25 mm) from x-ray detector 130 and/or object 40. UAV 110 is then rotated radially about object 40 while optical camera 140 is within visual range (e.g., can "see") of an optical pattern 150 that is attached to the side, above, or below x-ray detector 130. UAV 110 is maneuvered (e.g., pivoted) such that optical pattern 150 is within a field of vision of optical camera 140; this may be accomplished manually or via image recognition software and autonomous movement of UAV 110. X-ray source 120, x-ray detector 130, and optical camera 140 are activated substantially simultaneously, such that an x-ray image of at least a part of object 40 is captured at the same time an optical image containing optical pattern 150 is captured by optical camera 140. The relative positions of the optical pattern captured in the optical images are used to determine the imaging geometry present between x-ray source 120 and x-ray detector 130 for each activation of x-ray source 120 (e.g., each x-ray exposure). This imaging geometry information is used for tomography reconstruction of object 40 using the projection images.

In some embodiments, the object to be imaged is identified by operator commanding UAV 110. In some such embodiments, the location of object 40 and the trajectory of UAV 110 is defined by the operator providing inputs to a controller for UAV 110. The trajectory of UAV 110 is such that x-ray source 120 and x-ray detector 130 are, to a substantial degree, circulating and/or rotating radially around object 40. The total number of images of object 40 to be captured, the exposure time, and a distance from x-ray source 120 to x-ray detector 130 can be predetermined in an imaging protocol executed by UAV in capturing the x-ray and optical images. This imaging protocol can, for example, be stored in an electronic controller 114. Electronic controller 114 can be located remote from UAV 110 and configured for wireless communication with UAV 110, x-ray source 120, optical camera 140, and/or x-ray detector 130.

In some such embodiments where electronic controller 114 is remote from UAV 110, x-ray source 120, optical camera 140, and/or x-ray detector 130, electronic controller 114 can be configured as a cloud computing device and/or as a discrete device that is configured to communicate via a cloud computing device. In other embodiments, electronic controller 114 can be located within a vehicle controller 116 configured for wireless communication with UAV 110. In some other embodiments, electronic controller 114 can comprise at least two electronic controllers, a first electronic controller and a second electronic controller. In such embodiments, the first electronic controller may be configured to communicate (wired or wirelessly) with or be located on or in UAV 110 to control a movement of UAV 110, activation of x-ray source 120, and/or movement and/or activation of optical camera 140; the second electronic controller may be configured to communicate (wired or wirelessly) with or be located on or in x-ray detector 130 to control an activation of x-ray detector 120. In such embodiments, the second electronic controller may be in wireless communication with the first electronic controller so that the activation of x-ray source 120 may be synchronized and substantially simultaneous with (e.g., within 5 ms, 10 ms, 25 ms, 50 ms, and/or 100 ms) the activation of x-ray detector 130 and/or optical camera 140. In still other embodiments, electronic controller 114 may be configured to receive the plurality of x-ray projection images and corresponding optical images, perform geometric image correction to each of the plurality of x-ray projection images based on analysis of optical pattern 150 visible in the plurality of optical images captured by optical camera 140, and/or process the plurality of corrected x-ray projection images into a three-dimensional (3D) image of object 40 by executing an image reconstruction protocol (e.g., tomographic reconstruction). In one example, the locations relative to object 40 where x-ray source 120 is activated are substantially evenly divided long a trajectory of movement of UAV 110 around object 40. X-ray source 120 (e.g., x-ray exposure) is remotely activated. In some embodiments, data collection on x-ray detector 130 is activated by the x-ray photons from x-ray source 120.

In another example, to increase the angular coverage of the multiple x-ray projection images captured by x-ray detector 130, x-ray detector 130 is placed in multiple positions. For each position of x-ray detector 130, the above described process is repeated to capture a series of x-ray projection images. All the projection images are combined for image reconstruction of object 40.

Figure 4:
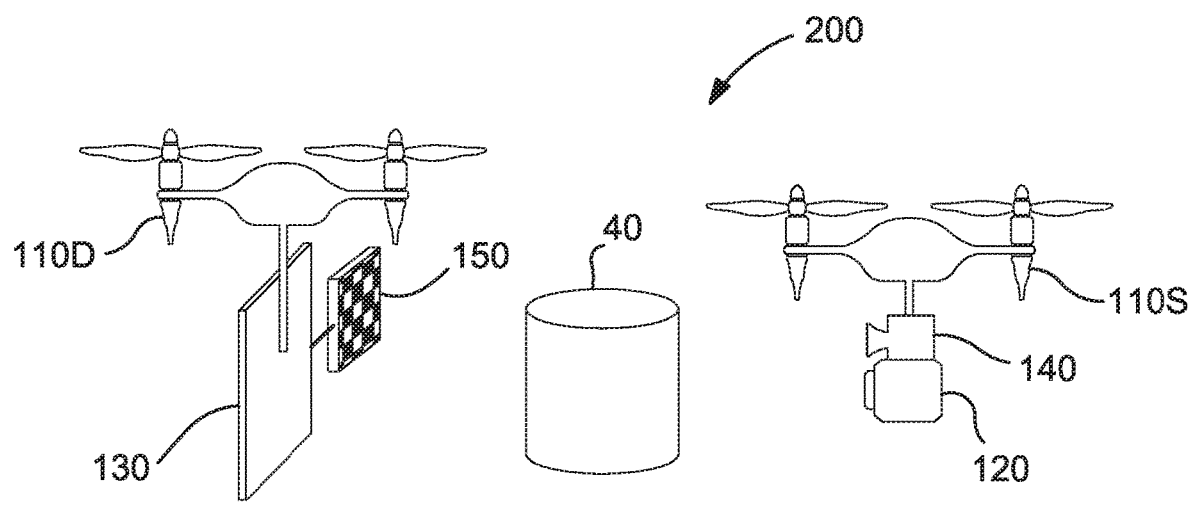
FIG. 4 is a schematic illustration of a second example embodiment of an aerial mobile x-ray imaging system for computed tomography image reconstruction, in accordance with the disclosure herein.

Referring now to FIG. 4, a second embodiment of a mobile aerial x-ray imaging system, generally designated 200, is shown. Imaging system 200 includes a source UAV 110S and a detector UAV 110D. As was discussed above for imaging system 100 in FIG. 3, source UAV 110S has an x-ray source 120 and optical camera 140 fixedly mounted to source UAV 110S in a fixed and known (e.g., calibrated position) relative to source UAV 110S. Detector UAV 110D has an x-ray detector 130 and an optical pattern 150 fixedly mounted to detector UAV 110D in a fixed and known (e.g., calibrated) position relative to detector UAV 110D. In such embodiments, the source and detectors UAVs 110S and 110D, respectively, are configured to navigate sufficiently close to object 40, and rotate radially around object 40 in a coordinated manner so that the position of source UAV 110S relative to detector UAV 110D is precisely known.

In some embodiments, an optical camera 140 is mounted on source UAV 110S and an optical pattern 150 is either attached to x-ray detector 130 mounted on detector UAV 110D or fixed at a known location on an outside of detector UAV 110D. Optical pattern 150 is a pre-defined pattern (e.g., a checkerboard pattern) with pre-defined image characteristics (e.g., spacing). In other embodiments, optical pattern 150 can be printed on or applied to an outer surface of detector UAV 110D as an image (e.g., painted on, adhesive decal, etc.). Optical camera 140 captures images of optical pattern 150 contemporaneously with the timing of the activation of x-ray source 120. The optical images are used to determine the imaging geometry for each x-ray exposure. This imaging geometry information is used for tomography reconstruction of object 40 using the projection images.

According to some embodiments for operating imaging system 200, object 40 is identified as the object to be imaged by an operator. In some embodiments, the location of object 40 and the trajectories of source and detector UAVs 110S and 110D are defined by the operator using one or more controllers. The trajectories of source and detector UAVs 110S and 110D are such that x-ray source 120 and x-ray detector 130, to a substantial degree, rotate radially around object 40. The total number of images of object 40 to be captured, the exposure time, and the distance of x-ray source 120 from x-ray detector 130 is predetermined in an imaging protocol stored on or transmitted to, then executed by, source and detector UAVs 110S and 110D. In one example embodiment, the locations where x-ray source 120 is activated are substantially evenly divided long a trajectory of movement of source UAV 110S around object 40. X-ray source 120 (e.g., x-ray exposure) is remotely activated. In one embodiment of this invention, data collection on x-ray detector 130 is activated by the x-ray photons from x-ray source 120.

In another embodiment, source and detector UAVs 110S and 110D may each be configured with one or more object detection sensors to estimate the distance between object 40 and source or detector UAVs 110S or 110D to automatically plan a substantially circular trajectory around object 40 with appropriate distances between x-ray source 120 and object 40, between object 40 and x-ray detector 130, and the distance between x-ray source 120 and x-ray detector 130, such that x-ray images of object 40 are completely or substantially captured by x-ray detector 130. The total number of images of object 40 to be captured, the exposure time, and the distance of x-ray source 120 from x-ray detector 130 are predetermined in an imaging protocol stored on or transmitted to, then executed by, source and detector UAVs 110S and 110D. In one example, the locations where x-ray source 120 is activated are substantially evenly divided along a trajectory of movement of source UAV 110S around object 40.

As source and detector UAVs 110S and 110D move around object 40, x-ray source 120 is activated, releasing x-ray radiation at least once at each location selected for imaging, and x-ray detector 130 is activated at least when x-ray source 120 is activated, so that the x-ray radiation emitted by source UAV 110S is captured as a projection image by x-ray detector 130. In some embodiments, x-ray source 120 and x-ray detector 130 may be activated at all times as they are moved by source and detector UAVs 110S and 110D, respectively, about object 40 so that a continuous pattern of projection images is obtained.

In such embodiments having an optical camera 140 mounted to source UAV 110S, source UAV 110S also has a wireless communication module for wireless transmission of the optical images to the operator terminal for use in geometry determination.

For each image taken, an optical image of optical pattern 150 connected to x-ray detector 130 is also recorded. These optical images are used to calculate the positions of x-ray source 120 and x-ray detector 130 with respect to each other. In addition, in embodiments where certain optical identifiable features of object 40 can be used as the reference world coordinate center, the optical images of object 40 are used to determine the relative positions of object 40 to x-ray source 120. This positioning information is used for image reconstruction.

While source and detector UAVs 110S and 110D with x-ray source 120 and x-ray detector 130, respectively, rotate around object 40, multiple images, both x-ray images and optical images, of object 40 are captured.

Figure 5:
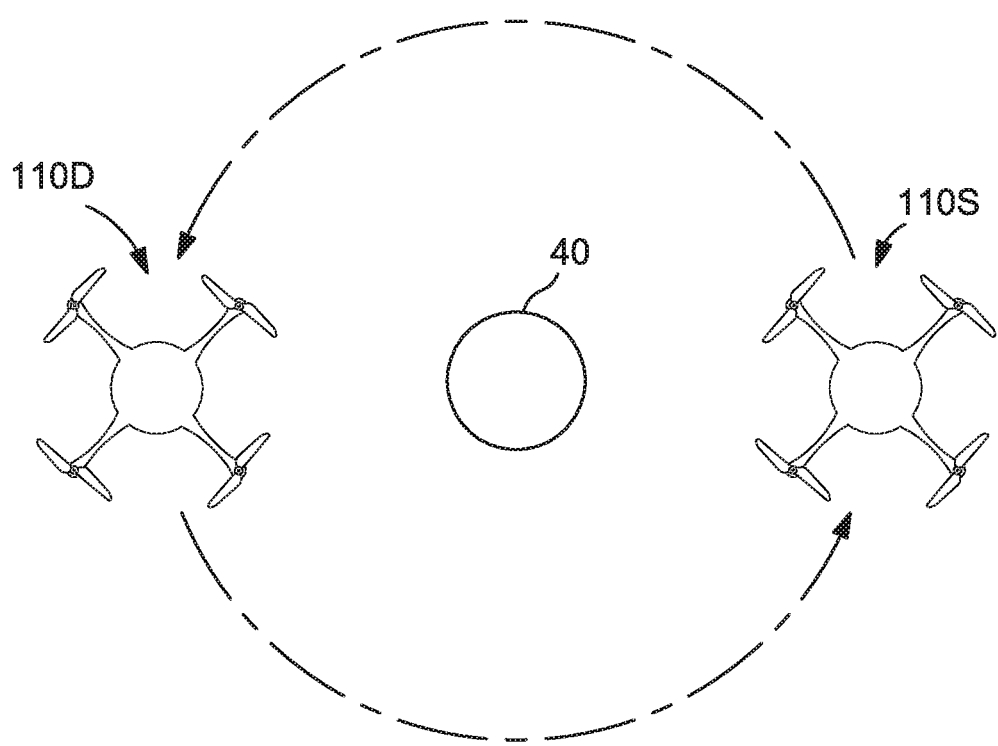
FIG. 5 shows an example transit path for the embodiment of the aerial mobile x-ray imaging system of FIG. 4, in accordance with the disclosure herein.

In one embodiment of this invention, the movements of source and detector UAVs 110S and 110D around object 40 follow the pre-defined trajectories programmed in vehicle controller 116. An example of such a trajectory path can be seen in FIG. 5, where source and detector UAVs 110S and 110D are shown rotating in a substantially circular pattern on opposite sides of object 40. The movement of source and detector UAVs 110S and 110D are such that they remain on opposite sides of object 40 while x-ray transmission images are being generated and captured. In one embodiment, certain easily identifiable surface features of object 40 are used as a reference world coordinate center, such that the trajectory of source and detector UAVs 110S and 110D around object 40 can be substantially circular around this coordinate center.

In one embodiment, the x-ray projection images of object 40 and the optical images of optical pattern 150 are transmitted to a base station through a wireless communication protocol (e.g., Bluetooth®, Wi-Fi, RF, etc.). Images of optical pattern 150 obtained by optical camera 140 are used to determine the imaging geometries. The 2D x-ray projection images are reconstructed into 3D computed tomography images of object 40. This reconstruction can be performed at the operator terminal or remotely by any suitable computing device, in which case the 3D computed tomography images would be transmitted for viewing at the operator terminal or any other suitable location.

In some embodiments, detector UAV 110D is equipped with a storage medium that retains the projection images captured by x-ray detector 130. These projection images can be retained for a specific period of time, deleted after confirmation of their transmission to an operator terminal, or kept indefinitely (e.g., until manually deleted or overwritten due to storage capacity limitations). The positions of x-ray source 120 and x-ray detector 130 for each of the projection images must be known.

Dual Energy CT

In another embodiment, two sets of x-ray images of object 40 are captured at two different energy levels for x-ray source 120. One set of x-ray images are captured at high x-ray energy level, the other set of x-ray images are captured at a low x-ray energy level. The two sets of images are used for dual energy CT reconstruction and for computing the effective density and the effective electron density of and within object 40. Dual energy CT enable provide the additional information needed for chemical identification by calculating both the density and the effective atomic number for each voxel reconstructed. This allow for detection of certain specific chemical materials such as explosive or nuclear hazard materials that may be hidden within the internal contents of object 40.

Backscatter

In another embodiment, x-ray detector 130 and x-ray source 120 remain on the same side of object 40; the backscattering images of object 40 are recorded at different viewing angles. In one embodiment, a collimator is used to collimate the x-ray radiation into a pencil beam.

Figure 6A:
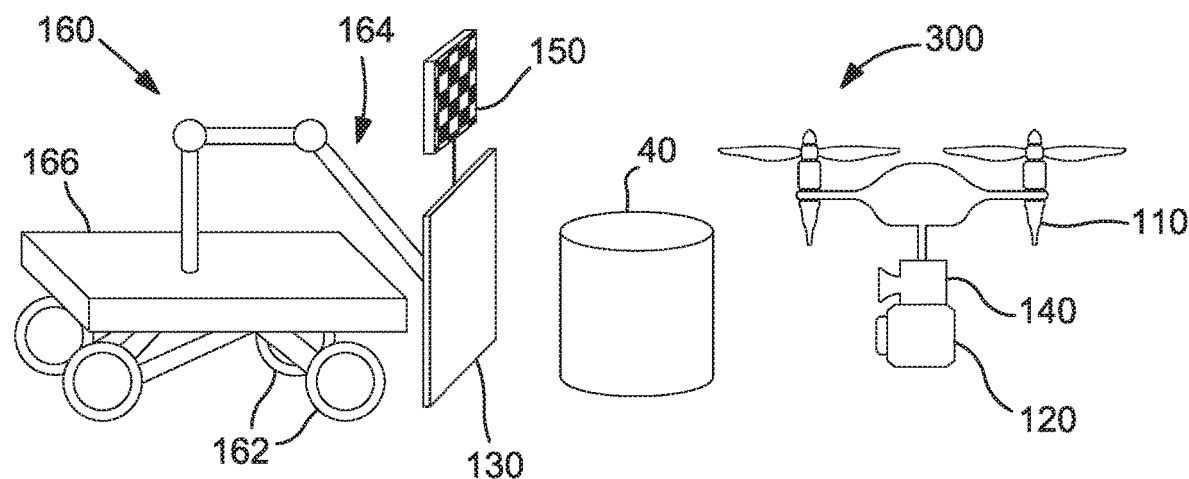
FIG. 6A is a schematic illustration of a third example embodiment of an aerial mobile x-ray imaging system for computed tomography image reconstruction, in accordance with the disclosure herein.

Referring now to FIG. 6A, another example embodiment of a remote imaging system, generally designated 300, is shown. Imaging system 300 has a wheeled trolley (e.g., an "unmanned vehicle," or UV), generally designated 160, that is used instead of detector UAV 110D. Wheeled trolley 160 moves by rotation of a plurality of wheels 162, which are each connected to a frame 166. An articulating arm 164 is rotatably connected to frame 166. X-ray detector 130 and optical pattern 150 are connected to and/or at a distal end of articulating arm 164. Just as was described relative to FIGS. 4 and 5, wheeled trolley 160 moves around object 40, adjusting a position of x-ray detector relative to object 40 by moving articulating arm 164 and/or moving wheeled trolley by turning and/or driving wheels 162. As such, wheeled trolley 160 is able to ensure that x-ray detector 130 and optical pattern 150 are rotated about object 40 so as to be located on a substantially diametrically opposite side (e.g., at least 135°) from x-ray source 120. UAV 110 operates substantially identically to the UAVs carrying x-ray source 120 and optical camera 140 in the embodiments discussed relative to FIGS. 3 through 5.

Figure 6B:
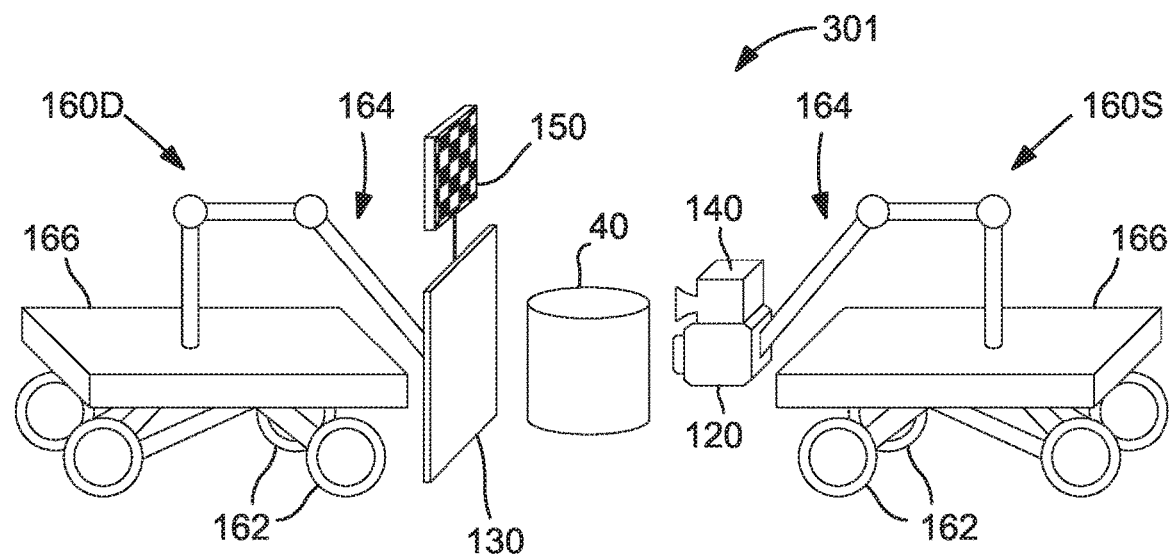
FIG. 6B is a schematic illustration of a fourth example embodiment of a mobile x-ray imaging system for computed tomography image reconstruction using unmanned vehicles, in accordance with the disclosure herein.

Referring now to FIG. 6B, still another example embodiment of a remote imaging system, generally designated 301, is shown. Imaging system 301 has two wheeled trolleys (e.g., "unmanned vehicles", or UV), a source trolley, generally designated 160S, and a detector trolley, generally designated 160D. Both source trolley 160S and detector trolley 160D move by rotation of a plurality of wheels 162, which are each connected to a frame 166. The movement of source trolley 160S and detector trolley 160D can be independent of or in coordination with each other. An articulating arm 164 is rotatably connected to frame 166 for both source trolley 160S and detector trolley 160D. Detector trolley 160D has x-ray detector 130 and optical pattern 150 connected to and/or at a distal end of its respective articulating arm 164. Source trolley 160S has x-ray source 120 and optical camera 140 connected to and/or at a distal end of its respective articulating arm 164. Just as was described relative to FIGS. 4 and 5, source trolley 160S and detector trolley 160D are configured to move around object 40. During this movement of source and detector trolleys 160S and 160D around and/or about object 40, the respective positions of x-ray source 120 (and optical camera 140) and of x-ray detector 150 relative to object 40 are adjusted and/or changed by respective movements of the respective articulating arms 164 and/or by turning and/or driving wheels 162 of source trolley 160S and/or detector trolley 160D.

In some embodiments, detector trolley 160D is moved to a position with x-ray detector 130 and optical pattern 150 held at a first position. In such embodiments, source trolley moves x-ray source 120 and optical camera 140 around object 40 while x-ray detector 130 and optical pattern 150 remain fixed in a position by detector trolley 160D. After x-ray source 120 captures all x-ray projection images possible and/or needed for a specific image reconstruction protocol specified, detector trolley 160D is configured to move x-ray detector 130 to another position, with optical camera taking an image of optical pattern before and after the movement of x-ray detector 130 (and optical pattern 150) before further x-ray projection images are captured so that the new position of optical pattern 150 and x-ray detector 130 can be determined for geometric image correction. One or both of source trolley 160S and detector trolley 160D can be configured to have an internal memory for storage of imaging instructions and/or x-ray projection images as well as optical images captured by x-ray detector 130 and optical camera 140, respectively.

In another embodiment, both the positions of x-ray source 120 (and optical camera 140) and x-ray detector 130 are moved between activations of x-ray source 120, x-ray detector 130, and/or optical camera 140. In such embodiments, after one of the plurality of x-ray projection images and optical images needed are captured, the positions of x-ray source 120, x-ray detector 130, optical camera 140, and/or optical pattern 150 are changed with respect to object 40 and/or to each other before another of the plurality of x-ray projection images and optical images needed are captured. This is repeated multiple times until all of the plurality of x-ray projection images and optical images needed for image reconstruction are captured.

In other embodiments, detector trolley 160D is configured to ensure that x-ray detector 130 and optical pattern 150 are rotated about object 40 so as to be located on a substantially diametrically opposite side (e.g., at least 135°) from x-ray source 120 and optical camera 140, which are maneuvered relative to object 40 and/or x-ray detector 130 and optical pattern 150 by source trolley 160S. In still other embodiments, source trolley 160S is configured to operate, through a movement of trolley and manipulation of x-ray source 120 and optical camera 140 using articulation arm 164, substantially similarly to UAV 110 in positioning x-ray source 120 and optical camera 140 in the embodiments discussed relative to FIGS. 3 through 6A.

While two wheeled trolleys are shown herein, it is contemplated that UAV 110 in the embodiment shown in FIG. 3 can be replaced with a source trolley 160S, such that detector 130 and optical pattern 150 are manually positioned and moved around object instead of being positioned by detector trolley 160D, as shown in FIG. 6B.

Figure 7A:
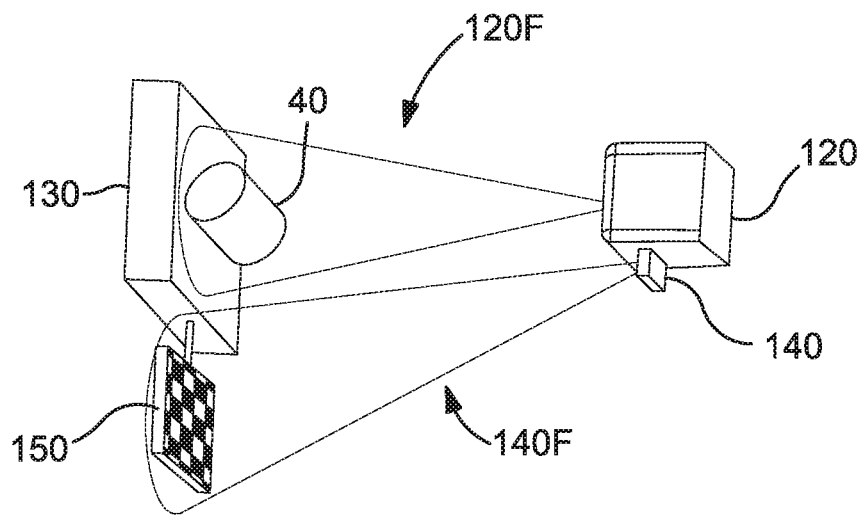
FIGS. 7A and 7B are different views of a schematic illustration of the imaging paths of an x-ray source and optical camera on a detector and optical pattern, respectively, in accordance with the disclosure herein.
Figure 7B:
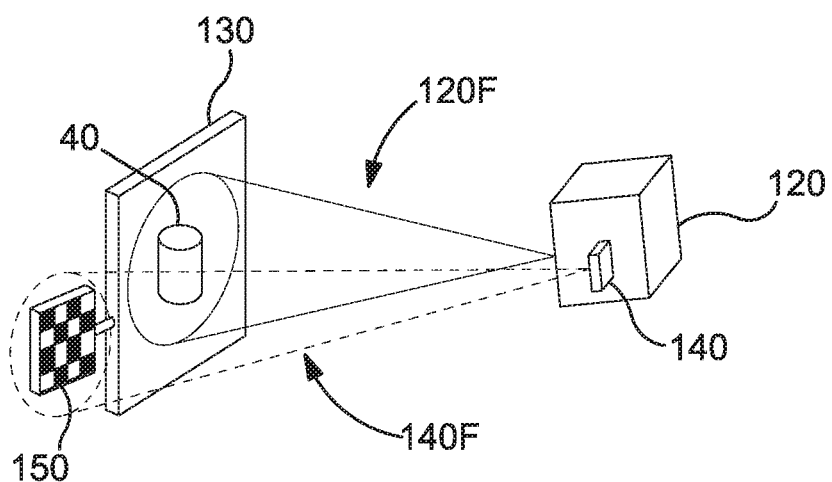

Referring now to FIGS. 7A and 7B, a schematic illustration of the relationship of x-ray source 120 and optical camera 140 relative to object 40, as well as x-ray detector 130 and optical pattern 150, is shown. FIG. 7A is a substantially top view, while FIG. 7B is a substantially side view. It is shown that x-ray source 120 emits an x-ray radiation patter, generally designated 120F, that is large enough to cast a projection image on x-ray detector 130. Similarly, optical camera 140, which is mounted to a side of x-ray source 120, is pointed such that it's field of view includes optical pattern 150.

Figure 8:
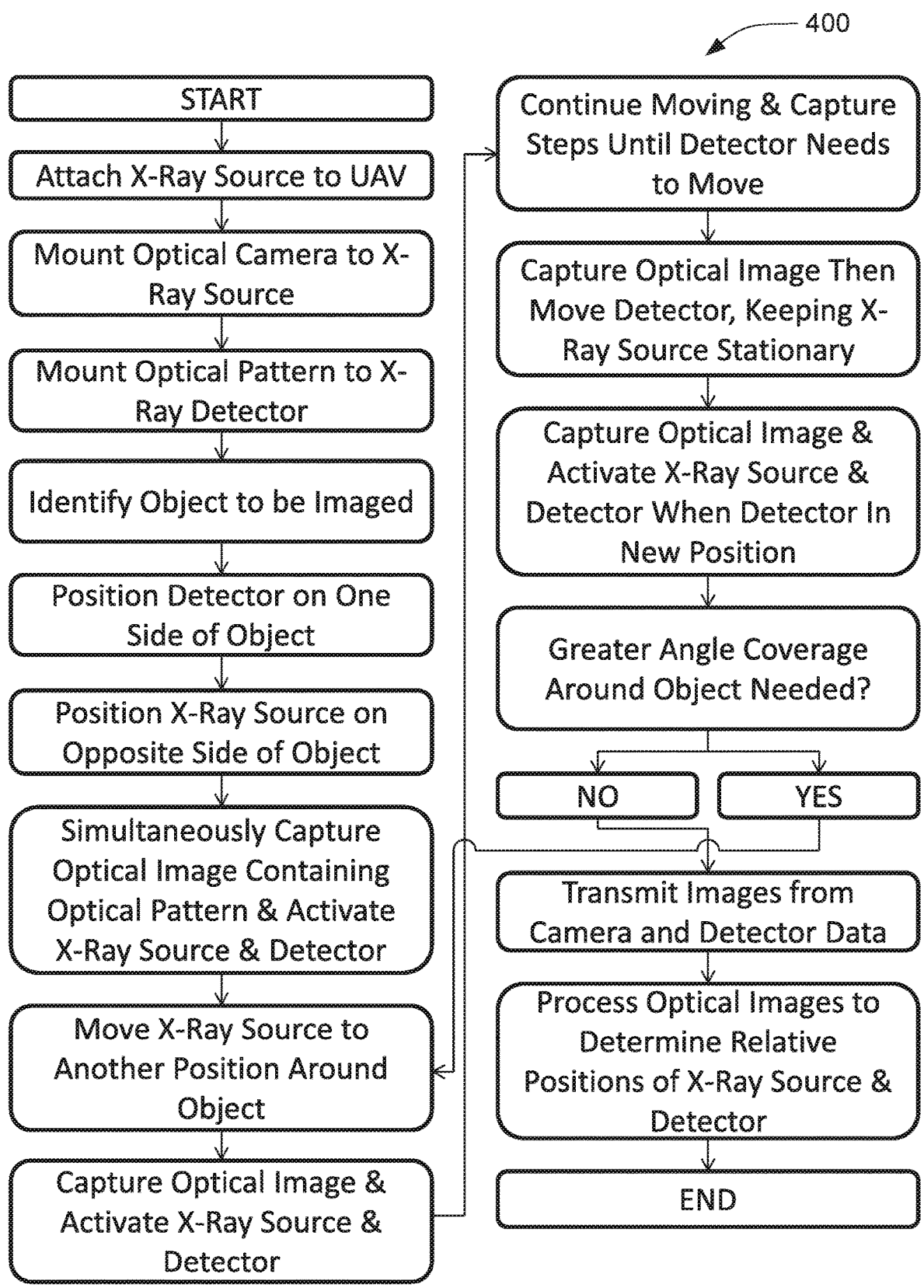
FIG. 8 is a flow chart of an example method of using an aerial mobile x-ray imaging system for computed tomography image reconstruction, in accordance with the disclosure herein.

Referring now to FIG. 8, a method of controlling a mobile aerial x-ray imaging system is shown via a flow chart as a series of steps. In a first step, an x-ray source is attached to a UAV. Next, an optical camera is mounted to the x-ray source (or the UAV). Then, an optical pattern is mounted to an x-ray detector. Next, the object to be imaged is identified by an operator. The x-ray detector is then positioned on a first side of an object. This x-ray detector may be positioned manually by an operator around an object of interest or may be mounted to a wheeled trolley or UAV (see, e.g., FIGS. 3 through 6). Next, the x-ray source is positions on a second side of the object, opposite the first side on which the x-ray detector is positioned. Now, the optical camera is positioned such that the optical pattern is within its field of vision and optical image(s) are captured with the optical camera simultaneously with an activation of the x-ray source and x-ray detector to generate and capture x-ray projection images. After the first image(s) are captured, the x-ray source is moved (e.g., rotated radially) around the object to one or more further positions around the object, where further optical and x-ray projection images are simultaneously captured. The above moving and capturing steps for the x-ray source are repeated until the x-ray detector needs to be moved to capture further x-ray projection images.

Before moving the x-ray detector, an optical image of the optical pattern is captured, then the x-ray detector is moved; during this time, x-ray source is maintained in a stationary position. Once the x-ray detector is in place again, an optical image containing the optical pattern is captured, while an x-ray projection image is simultaneously generated (e.g., by activating the x-ray source and the x-ray detector). If greater angle coverage of the object is needed for proper 3D image reconstruction, the x-ray source is moved and x-ray projection images and optical images are captured, repeating the steps of moving the x-ray detector as needed when the x-ray detector needs to be moved so that further imaging can be performed. Once no greater angle coverage around the object is needed, the optical and x-ray projection images are transmitted from the optical camera and x-ray detector, respectively. Finally, the optical images are processed visually to determine the relative positions of the x-ray source and x-ray detector, so that geometric correction can be applied to the x-ray projection images to de-skew these images for 3D reconstruction.

Figure 9:
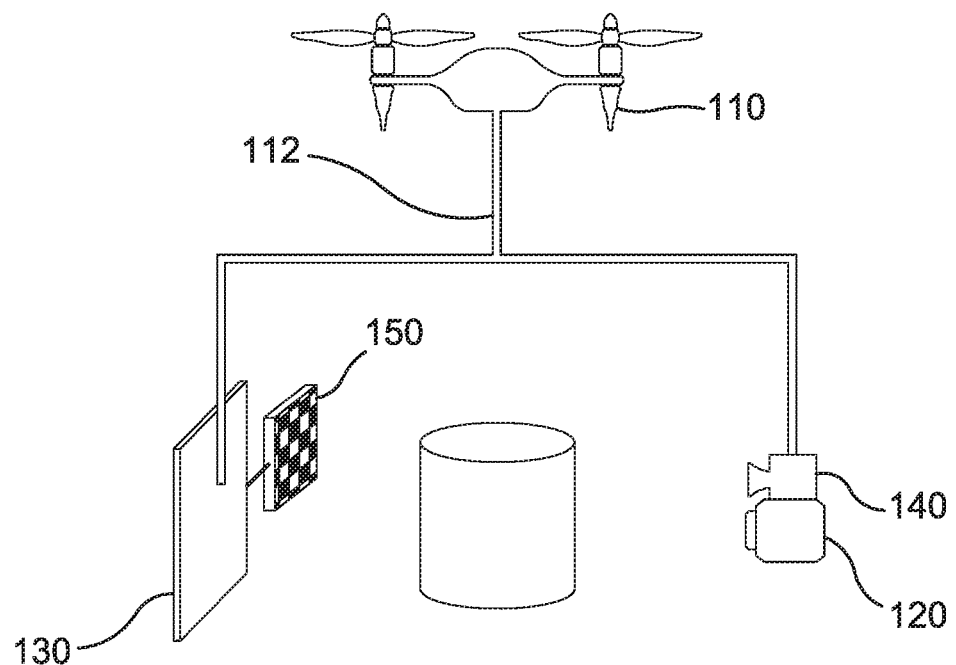
FIG. 9 is a schematic illustration of a fifth example embodiment of an aerial mobile x-ray imaging system for computed tomography image reconstruction, in accordance with the disclosure herein.

In another embodiment, shown in FIG. 9, x-ray source 120 and x-ray detector 130 are mounted on a single UAV 110. In one such embodiment, x-ray source 120 and x-ray detector 130 are mounted on opposite sides of a bracket 112 so as to be opposing each other at a fixed distance and angle.

To image an object, UAV 110 flies above object 40 with x-ray source 120 and x-ray detector 130 located on opposite sides of object 40. Different brackets may be used in order to accommodate objects of various sizes. UAV 110 spins around a fixed axis (e.g., a vertical central axis of object 40 and/or UAV 110) to cause x-ray source 120 and x-ray detector 130 to rotate around object 40 in a circular pattern. Multiple x-ray projection images of object 40 are recorded by x-ray detector 130 from multiple directions. At each location, an optical image of an optical pattern 150 fixed to x-ray detector 130, and/or optical images of object 40 are also recorded to calibrate the imaging geometry. The x-ray and optical images are transmitted to the base station through wireless transmission. Image reconstruction is performed to obtain a 3D image of object 40

The embodiments described herein are examples only and are not limiting. Many variations and modifications of the systems, apparatus, and processes described herein are possible and are within the scope of the disclosure. Accordingly, the scope of protection is not limited to the embodiments described herein, but is only limited by the claims that follow, the scope of which shall include all equivalents of the subject matter of the claims.

The invention claimed is:

1. A three-dimensional x-ray tomography imaging system, comprising:
   an x-ray source fixedly attached to a first unmanned aerial vehicle (UAV);
   an x-ray detector;
   a vehicle controller configured to be operated by an operator;
   an optical camera mounted to the first UAV at a fixed position relative to the x-ray source;
   an optical pattern fixed at a position relative to the x-ray detector; and
   an electronic controller configured for controlling the imaging system;
   wherein the vehicle controller is configured to transmit a sign to identify an object to be imaged,
   wherein the x-ray source and x-ray detector are configured to be positioned on substantially opposite sides of the object,
   wherein the x-ray source is configured to be rotated radially around the object to one or more imaging positions, and
   wherein the x-ray source and the x-ray detector are configured to be activated when the x-ray source is at each of the one or more imaging positions, so that x-ray projection images of the object are captured by the x-ray detector.

2. The system of claim 1, wherein the imaging system is configured for the x-ray projection images to be reconstructed to create a three-dimensional (3D) image of the object.

3. The system of claim 1, wherein the first UAV comprises a distance sensor configured to detect a distance from the first UAV to the object and/or the x-ray detector so that the first UAV can maintain a substantially consistent distance from the x-ray detector and/or the object.

4. The system of claim 1, wherein the x-ray source is configured to generate x-ray radiation at two different energy levels at each of the one or more imaging positions, so that the system can automatically classify and identify internal contents of the object.

5. The system of claim 1, wherein the x-ray detector and the optical pattern are fixedly mounted on a second UAV.

6. The system of claim 5, wherein the first and second UAVs are configured to automatically move to substantially opposite sides of the object to be imaged.

7. The system of claim 6, wherein the first and second UAVs are configured to rotate radially around the object to a plurality of imaging positions that are on substantially opposite sides of the object.

8. The system of claim 7, wherein the x-ray source and x-ray detector are activated at a same time at each of the plurality of imaging positions to generate one of a plurality of x-ray projection images at each of the plurality of imaging positions.

9. The system of claim 1, wherein the optical camera is configured to capture an optical image containing the optical pattern at a same position of the first UAV at which the x-ray source and the x-ray detector are activated.

10. The system of claim 1, wherein the x-ray detector and the optical pattern are mounted on a wheeled trolley configured to rotatably move the x-ray detector and the optical pattern around the object to be on a substantially diametrically opposite side of the object from the first UAV as the first UAV moves between the one or more positions.

11. The system of claim 1, wherein the x-ray detector and the optical pattern are fixedly mounted on a first side of a bracket attached to the first UAV, and wherein the x-ray source and the optical camera are fixedly mounted on a second side of the bracket attached to the first UAV.

12. The system of claim 11, wherein the bracket is configured to rotate about a central axis so that the x-ray source and the optical camera are configured to rotate radially around the object on substantially opposite sides of the object from the x-ray detector and the optical pattern while the bracket is rotating about the central axis.

13. A method of generating at least one three-dimensional (3D) image of an object from a plurality of x-ray images of the object, the method comprising:
mounting an x-ray source to a first unmanned aerial vehicle (UAV);
attaching an optical camera to the first UAV at a fixed position relative to the x-ray source;
identifying a location of the object;
positioning an x-ray detector and an optical pattern associated with the x-ray detector on a first side of the object;
moving the first UAV to a second side of the object, wherein the second side of the object is at least substantially diametrically opposite the first side of the object;
pointing the optical camera so the optical pattern is in a field of vision of the optical camera;
capturing an optical image and an x-ray projection image when first UAV is stationary;
rotating the first UAV around the object to a plurality of imaging positions around the object;
capturing further optical images and x-ray projection images at the plurality of imaging positions around the object, so that a plurality of optical images and a plurality of x-ray projection images are generated;
applying geometric image correction to the x-ray projection images by using the optical images; and
reconstructing the x-ray projection images to create a 3D image of the object.

14. The method of claim 13, comprising, when the optical pattern is no longer visible in the field of vision of the optical camera, moving the x-ray detector and the optical pattern to a further position around the object and generating further optical images and x-ray projection images by rotating the first UAV around the object to further imaging positions around the object.

15. The method of claim 13, comprising automatically classifying and identifying internal contents of the object by generating x-ray radiation at two different energy levels at each of the plurality of imaging positions.

16. The method of claim 13, wherein the first UAV uses a distance sensor to maintain a substantially consistent distance from the object at each of the plurality of imaging positions.

17. The method of claim 13, comprising:
attaching the x-ray detector and the optical pattern to a second UAV;
rotating the first and second UAVs radially around the object to a plurality of imaging positions, so the first and second UAVs are at substantially opposite sides of the object;
activating the x-ray detector and x-ray source to generate x-ray projection images of the object at each of the plurality of imaging positions; and
capturing optical images from the optical camera at each of the plurality of imaging positions,
wherein the optical pattern is within a field of vision of the optical camera at each of the plurality of imaging positions.

18. The method of claim 13, comprising:
mounting the x-ray detector and the optical pattern on a wheeled trolley; and
moving the x-ray detector and the optical pattern rotatably around the object to be on a substantially diametrically opposite side of the object from the first UAV as the first UAV moves between the one or more positions.

19. The method of claim 13, comprising:
mounting a bracket to the first UAV;
fixedly mounting the x-ray detector and the optical pattern on a first side of the bracket; and
fixedly mounting the x-ray source and the optical camera on a second side of the bracket.

20. The method of claim 19, comprising rotating the bracket about a central axis so that the x-ray source and the optical camera rotate radially around the object on substantially opposite sides of the object from the x-ray detector and the optical pattern.

21. A three-dimensional x-ray tomography imaging system, comprising:
an x-ray source fixedly attached to a first unmanned vehicle (UV);
an x-ray detector;
a vehicle controller configured to be operated by an operator;
an optical camera mounted to the first UV at a fixed position relative to the x-ray source;
an optical pattern fixed at a position relative to the x-ray detector; and
an electronic controller configured for controlling the imaging system;
wherein the vehicle controller is configured to transmit a sign to identify an object to be imaged,
wherein the x-ray source and x-ray detector are configured to be positioned on substantially opposite sides of the object,
wherein the x-ray source is configured to be rotated radially around the object to one or more imaging positions, and
wherein the x-ray source and the x-ray detector are configured to be activated when the x-ray source is at each of the one or more imaging positions, so that x-ray projection images of the object are captured by the x-ray detector.

22. A method of generating at least one three-dimensional (3D) image of an object from a plurality of x-ray images of the object, the method comprising:
mounting an x-ray source to a first unmanned vehicle (UV);
attaching an optical camera to the first UV at a fixed position relative to the x-ray source;
identifying a location of the object;
positioning an x-ray detector and an optical pattern associated with the x-ray detector on a first side of the object;

moving the first UV to a second side of the object, wherein the second side of the object is at least substantially diametrically opposite the first side of the object;

pointing the optical camera so the optical pattern is in a field of vision of the optical camera;

capturing an optical image and an x-ray projection image when first UV is stationary;

rotating the first UV around the object to a plurality of imaging positions around the object;

capturing further optical images and x-ray projection images at the plurality of imaging positions around the object, so that a plurality of optical images and a plurality of x-ray projection images are generated;

applying geometric image correction to the x-ray projection images by using the optical images; and reconstructing the x-ray projection images to create a 3D image of the object.

\* \* \* \* \*